(12) United States Patent
Shi et al.

(10) Patent No.: US 10,088,656 B2
(45) Date of Patent: Oct. 2, 2018

(54) STED SUPER-RESOLUTION MICROSCOPE AND ADJUSTING METHOD BASED ON A FIRST-ORDER BESSEL BEAM

(71) Applicant: Peking University, Beijing (CN)

(72) Inventors: Kebin Shi, Beijing (CN); Peng Xi, Beijing (CN); Wentao Yu, Beijing (CN); Qihuang Gong, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 15/755,072

(22) PCT Filed: Nov. 20, 2015

(86) PCT No.: PCT/CN2015/095118
§ 371 (c)(1),
(2) Date: Feb. 24, 2018

(87) PCT Pub. No.: WO2017/049752
PCT Pub. Date: Mar. 30, 2017

(65) Prior Publication Data
US 2018/0246308 A1 Aug. 30, 2018

(30) Foreign Application Priority Data

Sep. 23, 2015 (CN) .......................... 2015 1 0612186

(51) Int. Cl.
*G02B 21/00* (2006.01)
*G01N 21/64* (2006.01)

(52) U.S. Cl.
CPC ..... *G02B 21/0072* (2013.01); *G01N 21/6458* (2013.01); *G02B 21/0032* (2013.01); *G01N 2021/6463* (2013.01); *G02B 21/0036* (2013.01)

(58) Field of Classification Search
CPC ....... G01N 2021/6463; G01N 21/6458; G02B 21/0032; G02B 21/0036; G02B 21/0072
See application file for complete search history.

(56) References Cited

U.S. PATENT DOCUMENTS

2014/0347723 A1* 11/2014 Rafailov ............ G02B 21/0032
359/385

* cited by examiner

*Primary Examiner* — Mark R Gaworecki
(74) *Attorney, Agent, or Firm* — SV Patent Service

(57) ABSTRACT

A stimulated-emission-depletion (STED) super-resolution microscope includes an excitation light source, a depletion light source, an excitation light expanded beam alignment system, a spiral-shaped phase plate, a Bessel beam generating system, a depletion light focus lens, a beam combination system, an objective lens, a piezoelectric scanning system, a filter, a signal collection system, and a single-photon detector. The depletion light can be a first-order Bessel beam. The depletion light has anti-scattering and self-healing characteristics, and is capable of keeping the spot shape at a deeper position of a sample, thereby improving image resolution in the deep region of the sample. Compared to conventional STED super resolution microscope of deep-layer imaging using an adjustable correction collar, the present invention is simpler in experimental operations and does not require active adjustments. Compared to adaptive optical systems, the present experimental apparatus is simpler and less expensive.

10 Claims, 4 Drawing Sheets

STED SUPER-RESOLUTION MICROSCOPE AND ADJUSTING METHOD BASED ON A FIRST-ORDER BESSEL BEAM

TECHNICAL FIELD

The present invention relates to microscope techniques, and particularly to a STED super-resolution microscope based on a first-order Bessel beam (GB-STED), and adjusting method.

BACKGROUND OF THE INVENTION

Super-resolution microscopic imaging technique has a significant influence in biological imaging, material characterization, laser fine processing, etc. Among these, stimulated emission depletion (STED) microscope can realize super-resolution imaging by reducing the area of signal using a depletion beam, based on a conventional confocal microscope. Compared with other super-resolution imaging microscopies, STED microscope has a simple principle and can achieve super-resolution imaging of living objects in vivo, with fast imaging speed. STED super-resolution technique provides a new feasible method in biomedical research, nano-materials research, laser fabrication, optical storage, etc.

In conventional STED microscopy, there are two laser beams. One is an unmodulated Gaussian beam, called excitation beam. It can generate a nearly Airy spot after the focus by the objective lens, which can produce fluorescent signals by a fluorescent material at the focus area. The other beam, called depletion beam, is a Gaussian beam modulated by $0$-$2\pi$ vortex phase-plate. It can generate a doughnut shaped focal spot with a nearly zero intensity in the center. In the ring area of high depletion intensity, the excited molecules jump back to the ground state via stimulated emission instead of spontaneous radiation, so only the molecules in the dark center of depletion focal spot generate spontaneous radiation signals. Thus, the depletion beam can help obtain a super-resolution optical imaging. However, the shape of focal depletion spot is sensitive to the phase change. For specimens with large image depths, the resolution can rapidly decrease deep in the specimens because the shape of focal depletion spot is distorted due to spherical aberration, scattering distortion and loss.

In recent years, to improve deep imaging resolution in STED, some researchers achieved stable resolution at 80-100 micron image depth by adjusting a correction collar lens, but this method involves complex operations and is not suitable for high scattering samples. Some other efforts compensate spherical aberration with self-adaptive optics system, but these methods require complex operations or expensive optical system.

SUMMARY OF THE INVENTION

To solve the problems of deep super-resolution image in STED microscope, we present a method to achieve deep super-resolution imaging by using a first-order Bessel beam as a depletion beam. Owing to the anti-diffracting and self-healing nature of a Bessel beam, it is possible to obtain the constant imaging resolution deep in the scattering specimens.

One purpose of the present invention is to provide an improved STED super-resolution microcopy based on the first-order Bessel beam (GB-STED).

A presently disclosed GB-STED microscope includes an excitation laser source (continuous-wave or pulsed laser); a depletion laser source (continuous-wave or pulsed laser); an excitation collimating and beam expanding system; a depletion collimating and beam expanding system; a vortex phase plate; a Bessel beam generating system; a depletion beam focusing lens; a beam combining system; an objective lens; a piezoelectric scanning system; filters; a signal collecting system, and a single-photon detecting system. The excitation laser fills the entrance of the objective lens after passing the excitation collimating and beam expanding system. The linear-polarization depletion laser sequentially passes through the depletion collimating and beam expanding system, the vortex phase plate, the Bessel beam generating system, and the depletion beam-focusing lens. Then it is combined with the excitation beam and focused on the specimen. The specimen is placed on a piezoelectric scanning stage. Then super-resolution imaging of the specimen is obtained by collecting the signal via point scanning. The depletion beam focusing lens and the objective lens satisfy the confocal condition. The first-order Bessel beam through the Bessel generating system passes through the depletion beam focusing lens and the objective lens to produce a line-shaped focal spot along optical axial. The excitation beam generates a dot-shaped focal spot. We can make the dot-shaped excitation focal spot in the center of the line-shaped depletion focal spot along the optical axial by adjusting the distance between the Bessel generating system and the depletion beam focusing lens, which achieves precise overlapping in the cross-sections of the excitation beam and depletion beam.

The focusing lens of the depletion beam and the objective lens satisfy confocal conditions, forming a confocal system. The back focus of the depletion beam focusing lens is located near the front focus of the objective lens. The distance between the depletion beam focusing lens and the objective lens is adjusted to obtain the longest focused light spot along the axis.

The Bessel beam generating system can be implemented using an axicon. By adjusting the distance between the axicon and the depletion beam focusing lens, we can place the center of the dot-shaped excitation focal spot at the axial center of the line-shaped depletion Bessel beam. The length of the first-order Bessel beam passing the objective lens increases with the increased apex-angle of the axicon. Another method for the Bessel beam generating system is using an annular mask and a collimation lens. In this condition, the annular mask is placed in the front focal plane. The center of the dot-shaped excitation focus spot can be positioned at the axial center of the first-order Bessel beam by adjusting the distance between the two lenses besides the mask. The annular mask includes a transparent ring and an opaque base. The length of Bessel beam passing the objective lens has a negative correlation with the width of the ring. The width of the transparent ring is related to the axial length of the linear light beam generated by focusing the objective lens. The wider the transparent ring width, the longer the linear light beam. The Bessel beam generating system can be also a spatial light modulator (SLM). The center of the dot-shaped excitation focus spot can be positioned at the axial center of the first-order Bessel beam by adjusting the distance between SLM and the focus lens for the depletion beam.

The beam combining system contains a first dichroic mirror and a second dichroic mirror. The wavelength of the signal is located in the overlapping region of the transparent wavelength bands of the two dichroic mirrors. When the depletion beam is parallel with the excitation beam and the two beams are orthogonal with the signal beam, the first dichroic mirror is totally reflective for the depletion beam and totally transparent to the excitation beam and signal beam. The second dichroic mirror is totally reflective for the excitation beam and totally transparent to the signal beam. In this condition, the excitation beam and depletion beam are combined after being reflected respectively by the first and the second dichroic mirrors, and then focused on the samples by the objective lens. The signal beam passes through the two dichroic mirrors and comes into the single-photon detector. When the excitation beam and depletion beam are orthogonal and the depletion beam and the signal beam are parallel, the first dichroic mirror is totally reflective for the depletion beam and totally transparent to the excitation beam and signal beam. The second dichroic mirror is totally reflective for the signal beam and totally transparent to the excitation beam. In this condition, the depletion beam reflected by the first dichroic mirror is combined with the depletion beam after passing through the first and second dichroic mirror, and then focused on the samples by the objective lens. The reflected signal beam by the first dichroic mirror passes through the second dichroic mirrors and comes into the single-photon detector.

The signal collecting system contains a collecting lens and a multi-mode fiber as a confocal pinhole, which can eliminate the undesired signal from the area out of the focal spot to increase the axial resolution.

The depletion beam passes through the depletion beam-focusing lens and the objective lens, and then generates a line-shaped spot with the axial length over 20 μm. We can make the depletion beam and excitation beam overlapped in the axial direction by adjusting the distance between the Bessel beam generating system and the depletion beam-focusing lens. By adjusting the beam combining system, the overlapped precision of the two beams in the cross-section achieved is better than 10 nm.

Furthely, there is a half-wavelength plate between the vortex phase plate and the Bessel beam generating system, and a quarter-wavelength plate before the objective lens. We can adjust polarization of the depletion beam from linear to left-circular polarization to make sure a near-zero center of focused spot for highly signal-to-noise ratio.

Another objective of the invention is to provide adjusting methods for the above STED super-resolution microscope based on the first-order Bessel beam.

The presently disclosed method for adjusting a STED super-resolution microscope based on a first-order Bessel beam includes one or more of the following steps:

1) The excitation laser fills the entrance of the objective lens after the excitation collimating and beam expanding system. The depletion laser passes through a depletion collimating and beam expanding system, a vortex phase plate, a Bessel beam generating system, and a depletion beam-focusing lens in turns. Then it is combined with the excitation beam and focused on the specimen. The specimen is placed on a piezoelectric scanning stage. A super-resolution imaging of the specimen is obtained by collecting the signal via point scanning.

2) The excitation focal spot is placed at the center of the Bessel-shaped depletion spot along the axial direction by adjusting the distance between the Bessel generating system and the depletion beam-focusing lens.

3) Adjusting the beam combining system to achieve precise overlapping of the cross-section of the excitation beam and the depletion beam.

a) When the excitation beam and depletion beam are parallel to each other, it can make the two beam overlapped by titling the angle of the first and the second dichroic mirror to respectively change the deflection angle of the deletion beam and the excitation beam.

b) When the excitation beam and depletion beam are orthogonal to each other, it can make the two beam overlapped by titling the angle of the first dichroic mirror to change the deflection angle of the deletion beam.

4) Adjusting the distance between the depletion beam-focusing lens and the objective lens to achieve the longest axial length in the focused spot after the first-order Bessel beam passes the Bessel beam generating system and the depletion beam-focusing lens.

The disclosed STED microscope based on the first-order Bessel beam can be used as a single-photon or multi-photon microscope to improve the resolution in the deep areas of the specimen. Compared to conventional technologies, the disclosed system and method include the following advantages:

(1) The depletion beam can maintain its donut shape deep in the specimen because of its anti-diffractive and self-healing nature as the Bessel beam.

(2) Compared with the method of deep super-resolution imaging by adjusting the correction collar, the disclosed system and method do not need any active adjustments while imaging. On the other hand, compared with the adaptive optics systems, the disclosed system and method are simpler and less expensive.

DETAILED DESCRIPTION OF THE INVENTION

The present invention is described in more detail with the following implementation examples and the accompanying drawings.

Implementation Example One

Figure 1:
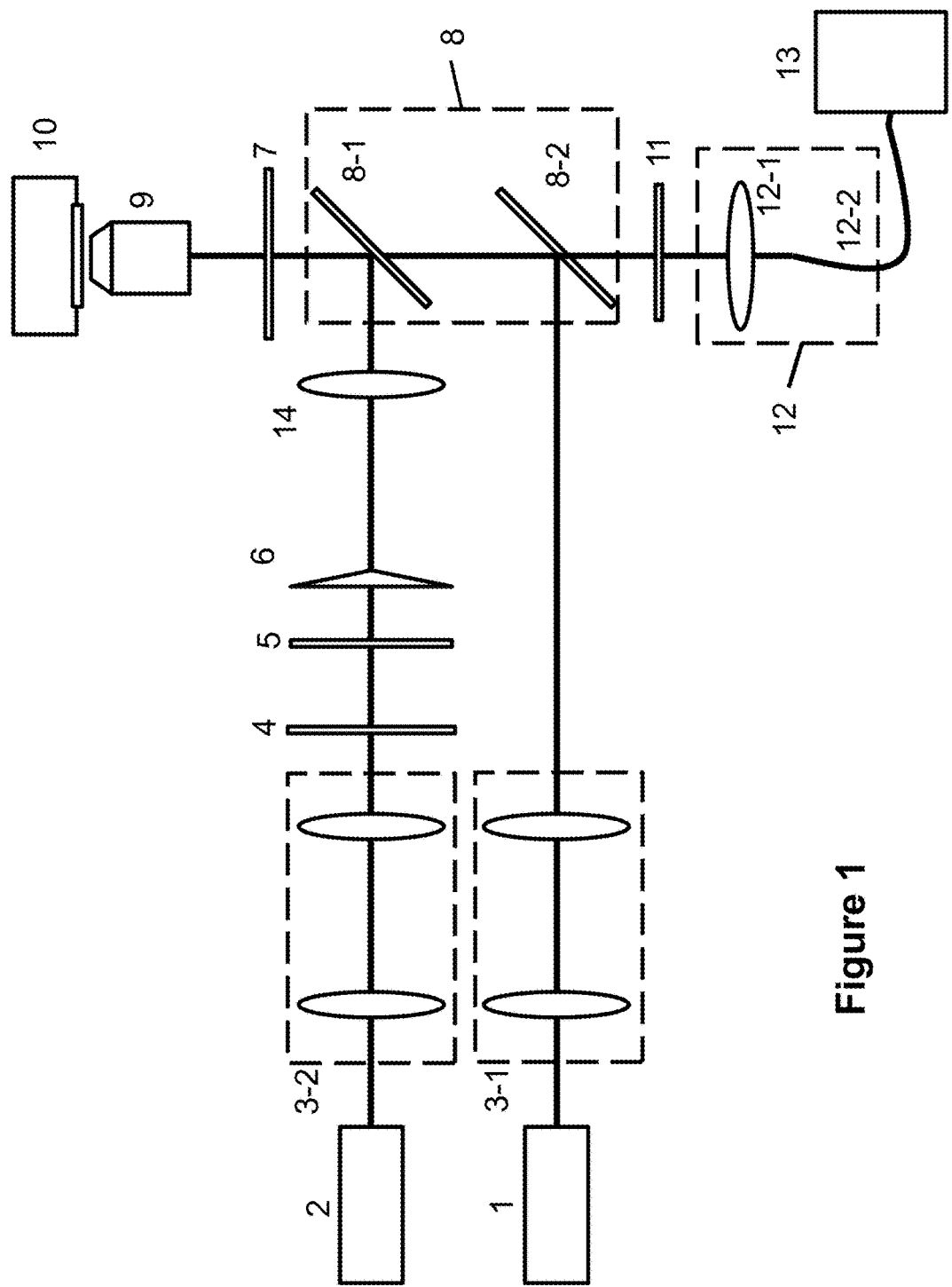
FIG. 1 is a schematic illustration of a GB-STED microscopy in Implementation Example One according to some embodiments of the present invention.

Referring to FIG. 1, a STED super-resolution microscopy based on the first-order Bessel beam includes: an excitation laser 1, a depletion laser 2, an excitation collimating and beam expanding system 3-1; a depletion collimating and beam expanding system 3-2; a vortex phase plate 4; a half-wavelength plate 5; a Bessel beam generating system 6; a depletion beam focusing lens 14; a beam combining system 8; an objective lens 9; a piezoelectric scanning system 10; a filter 11; a signal collecting system 12, and a single-photon detecting system 13. The excitation laser 1 fills the entrance of the objective lens 9 after the excitation collimating and beam expanding system 3-1. The linear-polarization depletion laser 2 passes through the depletion collimating and beam expanding system 3-2, the vortex phase plate 4, the half-wavelength plate 5, the Bessel beam generating system 6, and the depletion beam-focusing lens 14 in turns. Then it is combined with the excitation beam by the beam combining system 8 and focused on the specimen by the objective lens 9. The specimen is placed on a piezoelectric scanning system 10. The super-resolution imaging of the specimen is obtained by collecting the signal into the single photon detecting system 13 using the signal collecting system 12. In the current example, the depletion beam is parallel with the excitation beam and the two beams are orthogonal to the signal beam. The first dichroic mirror 8-1 is totally reflective for the depletion beam and totally transparent to the excitation beam and signal beam. The second dichroic mirror 8-2 is totally reflective for the excitation beam and totally transparent to the signal beam. In this condition, the excitation beam and the depletion beam are combined after being respectively reflected by the first dichroic mirror 8-1 and the second dichroic mirror 8-2, and then focused on the specimen by the objective lens 9. The signal beam passes through the two dichroic mirrors 8-1, 8-2 and comes into the single-photon detecting system 13 via the signal collecting system 12.

In the example, the Bessel beam generating system 6 is an axicon with the apex angle of 176 degree. The front focus of the depletion beam-focusing lens 14 (with a focal length of 200 mm) is overlapped with the center of the Bessel beam. The distance between the axicon and the depletion beam-focusing lens 14 is about 285 mm. The distance between depletion beam-focusing lens 14 and the objective lens 9 (60×, NA=1.2) is 202 mm. Under the above conditions, Bessel depletion beam passing the objective lens 9 has the longest length with a good beam profile in the cross-section.

The excitation laser 1 is 635 nm continuous-wave laser from a semi-conductor laser. The depletion laser 2 is a 750 nm continuous-wave laser from a Ti-sapphire laser. The diameter of the two beams reaches 8 mm and fills the entrance of the objective lens 9 after the collimating and beam expanding system. The two beams are combined by the beam combining system 8. The adjusting steps are shown as followings: the front focus of the depletion-focusing lens 14 is positioned near the center of the first-order Bessel depletion beam along the optical axial. Then the distance between the axicon 6 and the depletion-focusing lens 14 is adjusted to make sure the Gaussian excitation focal spot to lie at the center of the first-order Bessel depletion beam along the optical axial. By adjusting the angles of the first and second dichroic mirror in the beam combining system 8, we can achieve precise overlapping of the excitation and depletion focal spots in the cross-section. The front focus of the objective lens 9 is positioned near the back focus of the depletion-focusing lens 14. We can make sure that the length of Bessel depletion beam after the objective lens 9 is the longest with a good beam profile in the cross-section by adjusting the distance between the lens and objective lens.

Figure 3:
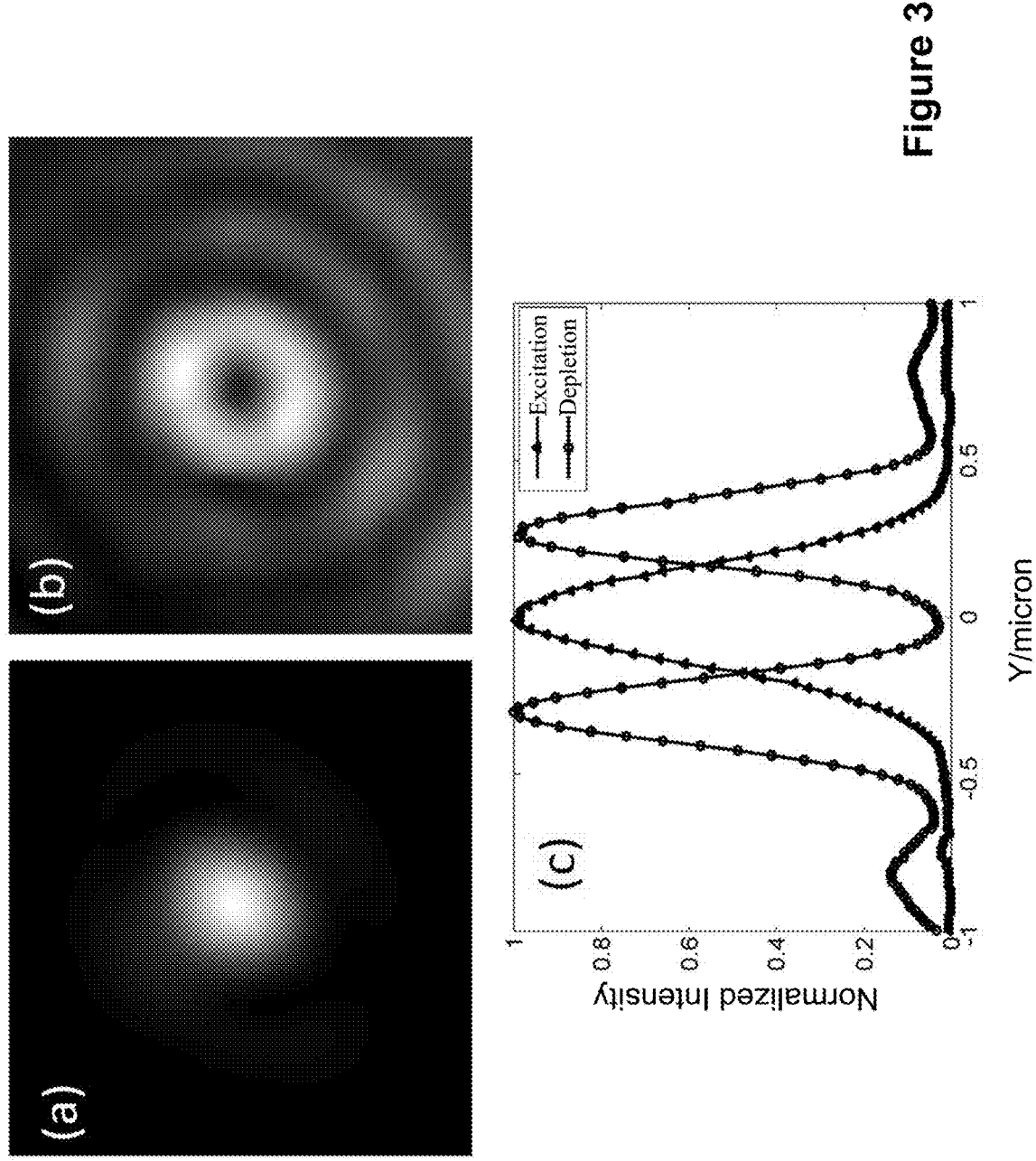
FIG. 3 shows a beam profile and an intensity distribution curve of the excitation beam and depletion beam at the focal plane in the GB-STED microscopy in Implementation Example One; (a) the beam profile of focused spot by the excitation beam; (b) the beam profile of focused spot by the depletion beam; (c) the intensity distribution curve of the excitation bean and the depletion beam along the Y direction.

The beam profiles of the excitation beam and depletion beam in the focal plane of the objective lens are shown in FIG. 3; (a) the beam profile of excitation beam; (b) the beam profile of depletion beam; (c) the intensity distribution curve of the excitation and depletion beams along the Y direction. The intensity in the center of the depletion focal spot is 3.7%, shown in FIG. 3(c), and the two beams are overlapped precisely.

Figure 4:
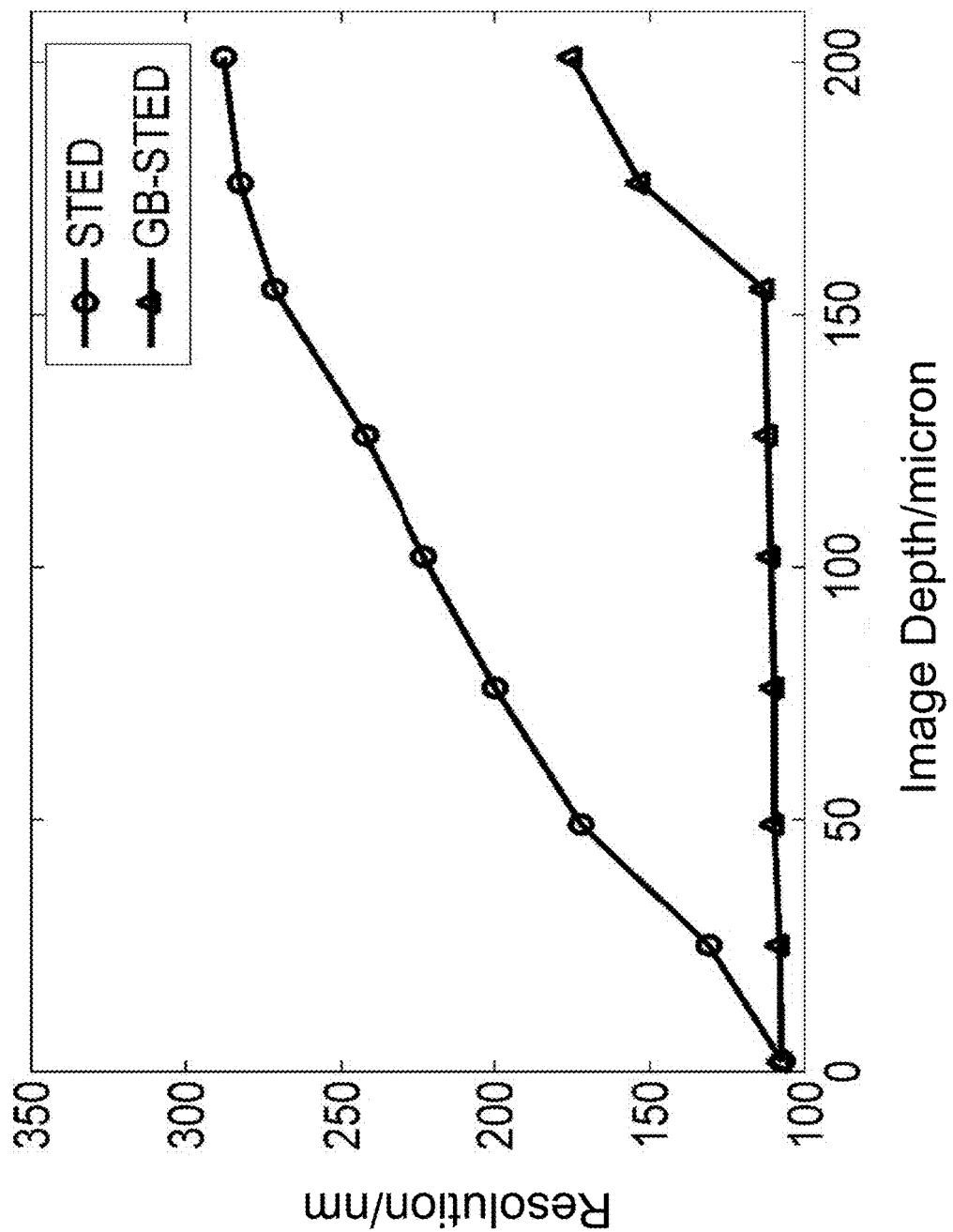
FIG. 4 shows the resolution vs the imaging depth via the GB-STED microscopy as implementation Example One in comparison with a conventional STED microscopy using agarose samples comprising 40 nm fluorescent beads.

FIG. 4 shows the resolution vs the imaging depth via the GB-STED microscopy described in Implementation Example One vs. a conventional STED microscopy using agarose gel samples comprising 40 nm fluorescent beads. The conventional microscopy has decreased resolution at larger imaging depth. The presently disclosed STED microscopy based on the first-order Bessel beam has a nearly constant resolution of 110 nm up to about 155 μm deep. Thus, it is shown that the deep image resolution is significantly improved when the depletion beam is implemented by a first-order Bessel beam.

Implementation Example Two

Figure 2:
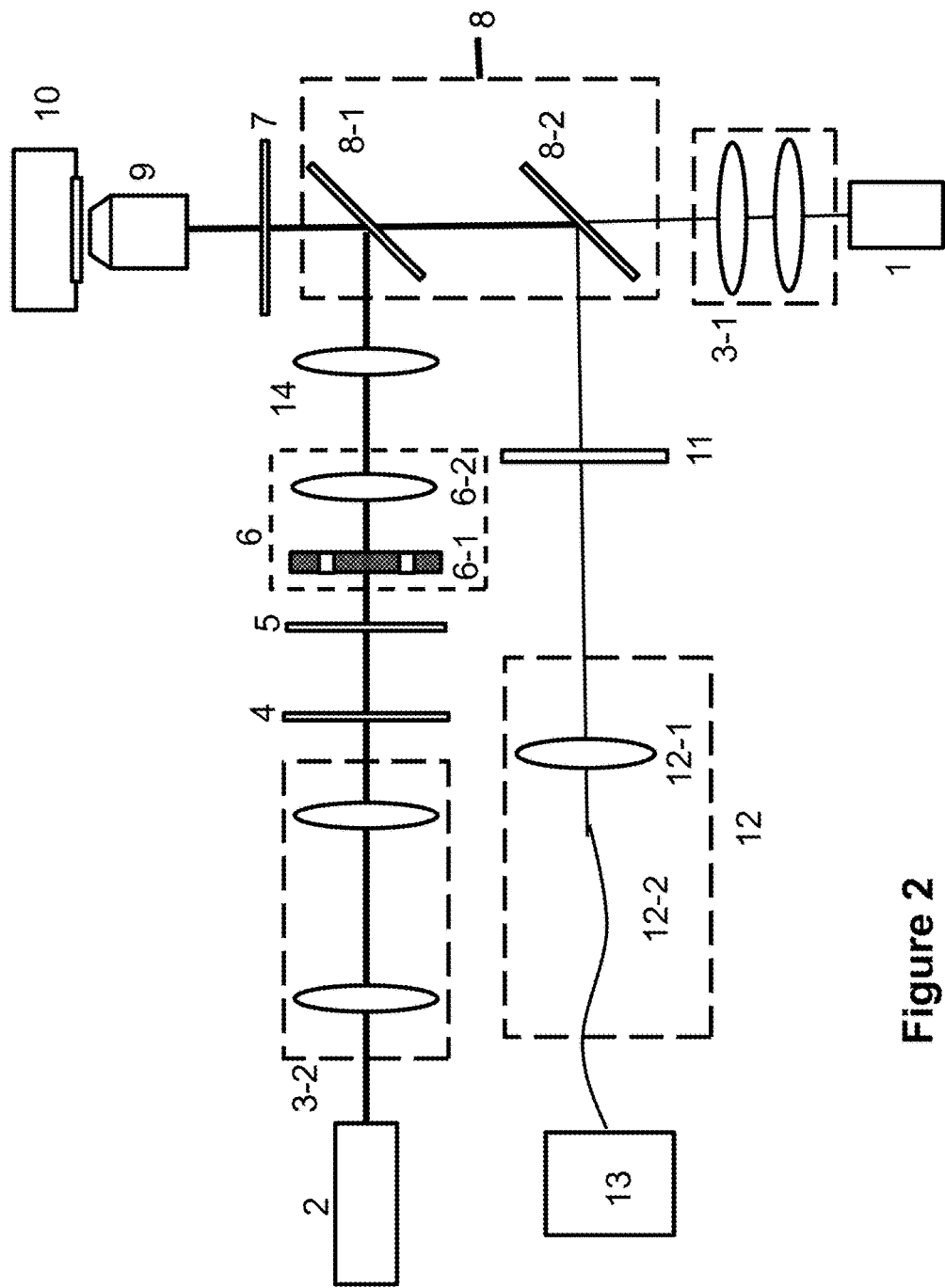
FIG. 2 is a schematic illustration of GB-STED microscopy in Implementation Example Two according to some embodiments of the present invention.

Referring to FIG. 2, the Bessel beam generating system 6 includes an annular mask 6-1 and a lens 6-2. We can adjust the distance between the lens 6-2 and the depletion beam-focusing lens 14 to make sure that the excitation focal spot to locate at the center of the first-order Bessel depletion beam. Then the excitation and depletion focal spot can be made to overlap precisely using the beam combining system 8.

In the current example, the excitation beam and depletion beam are orthogonal to each other; and the depletion beam and the signal beam are parallel to each other. The first dichroic mirror 8-1 is totally reflective for the depletion beam and totally transparent to the excitation beam and signal beam. The second dichroic mirror 8-2 is totally reflective for the signal beam and totally transparent to the excitation beam. In this condition, the depletion beam reflected by the first dichroic mirror 8-1 is combined with the excitation beam that has passed through the first and second dichroic mirror 8-1, 8-2, and then focused on the specimen by the objective lens 9. The signal beam passes through the first dichroic mirror 8-1 and next passes through the second dichroic mirror 8-2, and comes into the single-photon system 13 via the signal collecting system 12.

The above is a description of the current invention with reference to exemplary embodiments of the invention. One with ordinary skill in the art can readily recognize that various modifications could be made and alternatives to the exemplary embodiments can be used without departing from the scope and spirit of this invention. All such modifications and alternatives of the present invention are intended to be defined by the claims.

What is claimed is:

1. A STED super-resolution microscope based on a first-order Bessel beam, comprising:
    an excitation laser;
    a depletion laser;
    an excitation collimating and beam expanding system;
    a depletion collimating and beam expanding system;
    a vortex phase plate;
    a half-wavelength plate;
    a Bessel beam generating system;
    a depletion beam-focusing lens;
    a beam combining system;
    an objective lens;
    a piezoelectric scanning system;
    a filter;
    a signal collecting system; and
    a single-photon detecting system, wherein the excitation laser is configured to emit an excitation laser beam to pass the excitation collimating and beam expanding system and fill an entrance of the objective lens,
    wherein the depletion laser is configured to emit a linear-polarization depletion laser beam that sequentially passes through the depletion collimating and beam expanding system, the vortex phase plate, the Bessel beam generating system, and the depletion beam-focusing lens, wherein the depletion laser beam is combined with the excitation beam and focused on a specimen placed on a piezoelectric scanning stage, wherein a super-resolution imaging of the specimen is obtained by collecting the signal via point scanning, wherein the depletion beam-focusing lens and the objective lens are positioned in confocal conditions, wherein the first-order Bessel beam passes the Bessel generating system, and then passes through the depletion beam focusing lens and the objective lens to produce a line-shaped focal spot along optical axial, wherein the excitation beam generates a dot-shaped focal spot, wherein the dot-shaped excitation focal spot is positioned in the center of the line-shaped depletion focal spot along the optical axial by adjusting the distance between the Bessel generating system and the depletion beam-focusing lens, which precisely overlaps the excitation beam and depletion beam in cross-section.

2. The differential STED super-resolution microscope according to claim 1, wherein the Bessel beam generating system includes an axicon, wherein the distance between the axicon and the depletion beam-focusing lens is adjusted to place the dot-shaped excitation focal spot at the center of the line-shaped depletion Bessel beam along the optical axial, wherein a length of the first-order Bessel beam increases with increased apex-angle of the axicon.

3. The STED super-resolution microscope according to claim 1, wherein the Bessel beam generating system includes an annular mask and a collimation lens, wherein the annular mask is placed at a front focal plane, wherein the excitation and depletion spot are adjusted to overlap by adjusting the distance between the objective lens and the depletion beam-focusing lens.

4. The STED super-resolution microscope according to claim 3, wherein the annular mask includes a transparent ring and an opaque base, wherein a length of the first-order Bessel beam after passing the objective lens is negatively correlated with a width of the ring.

5. The STED super-resolution microscope according to claim 1, wherein the Bessel beam generating system includes a spatial light modulator (SLM), wherein the first-order Bessel beam and the excitation laser beam are adjusted to overlap along the optical axial by adjusting a distance between the SLM and the depletion beam-focusing lens.

6. The STED super-resolution microscope according to claim 1, wherein the beam combining system comprises a first dichroic mirror and a second dichroic mirror, wherein a wavelength of the signal is located in an overlap region of transparent wavelength bands of the first dichroic mirror and the second dichroic mirror.

7. The STED super-resolution microscope according to claim 6, wherein, when the depletion beam is parallel with the excitation beam, wherein the depletion beam and the excitation beam are orthogonal with a signal beam, wherein the first dichroic mirror is totally reflective to the depletion beam and totally transparent to the excitation beam and the signal beam, wherein the second dichroic mirror is totally reflective to the excitation beam and totally transparent to the signal beam, wherein the excitation beam and the depletion beam are combined after being respectively reflected by the first dichroic mirror and the second dichroic mirror and then focused on the specimen by the objective lens, wherein the signal beam passes through the first dichroic mirror and the second dichroic mirror and to be collected by the single-photon detector.

8. The STED super-resolution microscope according to claim 6, wherein, when the when the excitation beam and the depletion beam are orthogonal to each other, wherein the depletion beam and the signal beam are parallel, wherein the first dichroic mirror is totally reflective to the depletion beam and totally transparent to the excitation beam and signal beam; wherein the second dichroic mirror is totally reflective for the signal beam and totally transparent to the excitation beam, wherein the depletion beam reflected by the first dichroic mirror is combined with the depletion beam after passing through the first dichroic mirror and the second dichroic mirror, and then focused on the specimen by the objective lens, wherein the signal beam reflected by the first dichroic mirror passes through the second dichroic mirrors to be collected by the single-photon detector.

9. The STED super-resolution microscope according to claim 1, further comprising:
 a half-wavelength plate between the vortex phase plate and the Bessel beam generating system; and a quarter-wavelength plate before the objective lens,
 wherein polarization of the depletion beam is adjusted from linear to left-circular polarization.

10. A method for adjusting a STED super-resolution microscope according to claim 1, comprising the followings steps:
 1) filling the entrance of the objective lens by the excitation laser beam after the excitation laser beam passes the excitation collimating and beam expanding system; the linear-polarization depletion laser beam sequentially passing through the depletion collimating and beam expanding system, the vortex phase plate, the Bessel beam generating system, and the depletion beam-focusing lens; combining the linear-polarization depletion laser beam and the excitation beam and focused on the specimen placed on a piezoelectric scanning stage; obtaining a super-resolution imaging of the specimen by collecting the signal via point scanning;
 2) positioning the dot-shaped excitation focal spot at the center of the line-shaped depletion focal spot along the optical axial by adjusting the distance between the Bessel generating system and the depletion-beam focusing lens;
 3) adjusting the excitation beam and the depletion beam to overlap with each other in cross-section by adjusting the beam combining system:
  a) when the excitation beam and depletion beam are parallel, adjusting the excitation beam and the depletion beam to overlap with each other by titling the first dichroic mirror and the second dichroic mirror to respectively change deflection angles of the deletion beam and the excitation beam; or
  b) when the excitation beam and depletion beam are orthogonal to each other, adjusting the two beam overlapped by titling the first dichroic mirror to change a deflection angle of the deletion beam; and
 4) maximizing a length of focused spot of the first-order Bessel beam in the axial direction by adjusting a distance between the depletion beam-focusing lens and the objective lens.

* * * * *